United States Patent [19]

Esquivel H.

[11] Patent Number: 4,886,965
[45] Date of Patent: Dec. 12, 1989

[54] METHOD FOR CALIBRATING VARIABLE WAVELENGTH LIQUID CHROMATOGRAPHY DETECTORS

[75] Inventor: J. Benjamin Esquivel H., Midland, Mich.

[73] Assignee: The Dow Chemical Company, Midland, Mich.

[21] Appl. No.: 229,574

[22] Filed: Aug. 8, 1988

[51] Int. Cl.$^4$ .................... G01D 18/00; G01N 31/00; G01J 1/02; G01J 3/00
[52] U.S. Cl. ................... 250/252.1 A; 436/8; 436/19; 356/300; 356/243
[58] Field of Search .............. 250/252.1 A; 356/49, 356/243; 436/8, 19, 161; 422/70

[56] References Cited

U.S. PATENT DOCUMENTS

| | | | |
|---|---|---|---|
| 4,439,347 | 3/1984 | Sun et al. | 250/252.1 A |
| 4,461,718 | 7/1984 | Kaye et al. | 250/252.1 A |
| 4,533,518 | 8/1985 | Hanaoka et al. | 422/70 |
| 4,575,424 | 3/1986 | Allington et al. | 422/70 |
| 4,692,621 | 9/1987 | Passaro et al. | 250/252.1 A |
| 4,836,673 | 6/1989 | Esquivel | 356/300 |

OTHER PUBLICATIONS

J. C. Barnes, "Stability Constants and Spectra of Some Lanthanide Complexes," J. Chem. Soc. 1964, pp. 3880–3885.
K. Jorgensen, "Electron Transfer Spectra of Lanthanide Complexes," Mol. Phys. (5) 1962, pp. 271–277.
Therald Moeller and J. Calvin Brantley, "The Rare Earths," Analytical Chemistry, vol. 22, No. 3, Mar. 1950, pp. 433–441.
D. C. Stewart and Dorothy Kato, "Analysis of Rare Earth Mixtures by a Recording Spectro-photometer," Analytical Chemistry, vol. 30, No. 2, Feb. 1958, pp. 164–172.
National Bureau of Standards Certificate, Standard Reference Material 2034, Holmium Oxide Solution Wavelength Standard from 240 to 650 nm, Jun. 20, 1985.

Primary Examiner—Janice A. Howell
Assistant Examiner—Jacob Eisenberg
Attorney, Agent, or Firm—Timothy S. Stevens; Burke M. Halldorson

[57] ABSTRACT

A method for determining the wavelength accuracy of a variable wavelength liquid chromatography detector in the low UV range comprising filling the cell of the detector with a test solution and varying the indicated wavelength of detection to find the indicated wavelength of maximum absorbance in a wavelength region around a reference wavelength of the test solution and then calculating the difference between the indicated wavelength of maximum absorbance and the reference wavelength to determine the accuracy of the indicated wavelength of the detector. The test solution contains terbium III ions in a solvent such as n-propanol so that the absorbance maximum of the test solution does not shift more than about 0.5 nm for a spectral bandpass ranging from 2 to 6 nm.

7 Claims, No Drawings

METHOD FOR CALIBRATING VARIABLE WAVELENGTH LIQUID CHROMATOGRAPHY DETECTORS

FIELD OF THE INVENTION

The invention is in the field of methods used to calibrate the accuracy of wavelength selection of variable wavelength spectrophotometers.

BACKGROUND OF THE INVENTION

Liquid chromatography is an important branch of analytical chemistry. Most liquid chromatography systems include a spectrophotometer detector and a high proportion of these detectors are of the type where the wavelength of detection can be selected at will within a given range, i.e. the variable wavelength type of detector. Problems with variable wavelength detectors in liquid chromatography can occur if the actual wavelength of detection is different than the detector's set wavelength. For example, linearity of detection and selectivity of detection can deteriorate if the liquid chromatographic procedure is actually being run at one wavelength while the procedure calls for detection at another wavelength. Even when a variable wavelength detector is accurately calibrated when new, its wavelength accuracy can deteriorate with time. Within the spectral range of such detectors, the low UV zone (190-225 nm) is very often used to obtain a more general response and to enhance detector sensitivity for compounds containing weakly absorbing chromophores. Unfortunately, most organic compounds exhibit steeply sloping absorption bands in this wavelength range. Because of this fact, small wavelength differences, e.g., 3 nm, can cause large effects on the chromatographic results. Therefore, there is an important need to determine the accuracy of wavelength selection of variable wavelength liquid chromatography detectors in the low UV range.

The need to check the accuracy of wavelength selection is also important for general laboratory spectrophotometers and specific test solutions have been discovered for the calibration of general laboratory spectrophotometers such as the rare earth ion solution described in U.S. Pat. No. 4,461,718 to Kaye et al. Rare earth compounds are generally considered to be excellent candidates for the preparation of accuracy standards for variable wavelength spectrophotometers because solutions of rare earth ions often absorb light in very sharp bands as shown, for example, by Moeller et al. in Volume 22, No. 3, March 1950, pages 433-441 of *Analytical Chemistry* and by Stewart et al. in Volume 30, No. 2, February 1958, pages 164-172 of *Analytical Chemistry*. The patent and literature references, above, are fully incorporated herein by reference.

The prior rare earth test solutions developed for general laboratory spectrophotometers did not provide acceptable performance for variable wavelength liquid chromatography detectors because of the different optical characteristics of variable wavelength liquid chromatographic detectors. For example, the optical bandpass of most of these detectors is not adjustable and is different for different detector brands (generally ranging from about 2 nm to about 6 nm). The absorption bands of many rare earth ions in solution shift in absorbance maximum with a variation in optical bandpass, e.g., terbium III dissolved in water shifts from 219.4 to 218.6 nm when the bandpass changes from 2 to 6 nm. Another problem with these detectors is that it is more difficult to locate an absorption maximum by varying the wavelength selector of the detector since variable wavelength liquid chromatography detectors are generally designed to operate at one selected wavelength and are not designed to be scanning instruments. Therefore, the absorbance maximum of a test solution for variable wavelength liquid chromatography detectors must be intense or the maximum will not be found (and this is especially true for single beam variable wavelength detectors). For example, the well known holmium III test solution absorbance intensities at 241.1, 278.2 and 287.5 nm are too weak for use with most variable wavelength liquid chromatographic detectors.

SUMMARY OF THE INVENTION

However, it has been discovered that if terbium III salts are dissolved in certain solvents, then the shift in absorbance maximum of the terbium III ion in the low UV region with a variation in optical bandpass can be minimized relative to dissolving the terbium III salt in water.

The present invention is a method of determining the wavelength accuracy of a variable wavelength liquid chromatography spectrophotometric detector in the low UV range, the detector having a flow through detection cell and a means to vary the indicated wavelength of detection, which method comprises the steps of: (a) flowing a solution of terbium III ions in a noninterfering solvent into the cell, the solution having a detectable concentration of terbium III ions: (b) varying the indicated wavelength of detection to find the indicated wavelength of maximum absorbance of the solution in a wavelength region around a predetermined reference wavelength for terbium III in the solvent: and (c) calculating the difference, in units of nm, between the indicated wavelength of maximum absorbance of step (b) and the reference wavelength of step (b) to determine the accuracy of the detector at the reference wavelength of step (b).

DETAILED DESCRIPTION OF THE INVENTION

The method of the present invention comprises flowing the test solution into the flow cell of a normally operating variable wavelength liquid chromatography spectrophotometric detector by, for example, first flushing the cell with about 5 ml of water, then with the solvent of the test solution and then with about 1 ml of the test solution using a syringe, leaving the cell filled with the test solution. If the detector is a double beam detector and has a reference cell, the reference cell preferably contains air or better yet the solvent of the test solution The test solution allows the testing of the accuracy of the indicated wavelength of the detector at a specific reference wavelength in the low UV range. The reference wavelength tends to be somewhat different for different solvents as discussed in greater detail below. The indicated wavelength of the detector is varied in, for example, 0.5 or 1 nm increments around the reference wavelength (usually from 210 to 230 nm) to find the indicated wavelength of maximum absorbance as shown on some detectors by an absorbance window readout or for most any detector by a maximum pen response on a conventional strip chart recorder connected to the detector. The indicated wavelength of maximum absorbance of the test solution is compared to the reference wavelength of the test solution to determine the wavelength accuracy of the detector. For example, if the indicated wavelength of maximum absorbance of the test solution is 220.5 nm and the reference wavelength of the test solution is 218.5, then the detector is inaccurate by 220.5–218.5 nm or about 2 nm at 218.5 nm.

The ease of the determination of the wavelength of maximum absorbance is a function of the intensity of absorption of the test solution for any given detector. Preferably, the intensity of absorption is as high as practical but not higher than about 2.5 absorbance units, e.g., the use of about 0.01 molar terbium III with many detectors. If the intensity of absorption of the test solution is too high, above an absorbance of about 2.5, then the detector tends to saturate and give inaccurate results. However, not all terbium compounds are soluble enough to generate a 0.01 molar solution of terbium III ions and weaker solutions such as 0.006 molar terbium III have been shown to be satisfactory. The lowest concentration of a terbium III solution that would be useable depends on the characteristics of the specific detector being tested and below a "detectable concentration" it is not possible to find the indicated wavelength of maximum absorbance. Thus, the term "detectable concentration" means a concentration that results in an absorbance of less than 2.5 but not so low that it is not possible to find the indicated wavelength of maximum absorbance. With many detectors the lower concentration of terbium III that is a "detectable concentration" is about 0.002 molar. If the detector is a double beam detector and has a reference cell, then filling the reference cell with the solvent of the test solution helps to correct for the absorbance of the solvent in the low UV range and allows a somewhat more concentrated test solution. However, many detectors do not have a reference cell. Preferably, the terbium III compound used is terbium III perchlorate which has a relatively high solubility and results in test solutions that are stable upon extended storage in a hermetically sealed container. Preferably, the anion of the terbium III cation and the solvent itself are transparent in the test solution at the reference wavelength. However, the anion and solvent can absorb some light at the reference wavelength.

The solvent used to dissolve the terbium III ion is critical in the present invention. The solvent must be a "noninterfering solvent," i.e., the adsorption band of the terbium III ion dissolved in such a solvent must not shift in the low UV region by more than about 0.5 nm with a change in optical bandpass of from 2 to 6 nm. Whether a solvent for a given test solution is a "noninterfering solvent" can be readily determined by scanning the test solution in a high quality recording variable wavelength UV spectrophotometer (such as a Perkin Elmer model 330 UVVIS having a model 3600 data station) in the low UV range at an optical bandpass of 2, 4 and 6 nm. If the adsorption band shifts about 0.5 nm or less (preferably 0.3 nm or less) in such a test, then the solvent is a nondetrimental solvent. This test also indicates the absorption maximum of the terbium ion in the solvent which varies somewhat depending on the specific solvent, generally in the range of from about 215 to 220 nm. Water, methanol, and sec-butanol are not suitable as solvents in the present invention. Different noninterfering solvents can be mixed together if desired, e.g., a mixture of n-propanol and isopropanol. A noninterfering solvent can contain some water, methanol and sec-butanol (or other such solvent) but not so much that the absorption band of terbium III shifts more than 0.5 nm when the optical bandpass varies from 2 to 6 nm. Solvents known to be noninterfering solvents are ethanol, n-propanol, n-butanol, 2-propanol, 1,2-propanediol, tetrahydrofuran, 2-methoxyethylether, 2-ethoxyethanol, and 2-methoxyethanol. Among the more preferred solvents are ethanol, n-propanol, n-butanol, 1,2-propanediol and 2-methoxyethanol. The most preferred test solution is one containing about 3.6 milligrams of terbium perchlorate hexahydrate per milliliter of n-propanol. It has been found that each batch of test solution should be checked for its reference wavelength because some batches of solvent apparently affect the reference wavelength somewhat, probably because of trace impurities. Terbium perchlorate hexahydrate is available from Alfa Chemicals and n-propanol is available from many sources such as Burdick and Jackson or Fisher Scientific. Perchlorate salts and acids can be hazardous in contact with organic materials. The preferred test solution of the present invention is relatively dilute with regard to perchlorate ion but a leak or spill could concentrate the perchlorate ion. Precautions with regard to the safe use of perchlorate salts and perchloric acid are available and should be followed.

The test solution of the present invention can be prepared for use at a later time. The test solution in this event should be packaged in a hermetically sealed container in order to ensure the integrity of the solution Preferably, the sealed container is a borosilicate glass vial having a Teflon ® lined screw cap (such as vial number H3528 and cap number H3573 available from the Anspec Co., Ann Arbor, Mich.) which vial and cap are specifically designed and recognized for the storage of reagents and standards. Another preferred sealed container is a borosilicate glass vial having a Teflon lined crimped septum (such as vial number H3579, septum number A3284 and crimp collar A4697, available from the Anspec Co.). Containers comprising materials other than borosilicate glass and Teflon can also be used such as various plastic bottles and caps as long as they are not chemically attacked by the test solution and do not result in contamination of the test solution by, for example, the leaching of a contaminant from the container that would significantly interfere at a reference wavelength of the test solution. The hermetically sealed container should be labeled as to its contents and hazards. In addition, the label can contain instructions for the use of the contents to determine the wavelength accuracy of a variable wavelength liquid chromatography detector in the low UV range.

EXAMPLE 1

A terbium III perchlorate in n-propanol solution is prepared using Alfa Chemicals 99.9% grade terbium III perchlorate hexahydrate dissolved in Fisher Scientific Co. ACS Certified grade n-propanol (3.6 milligrams of terbium perchlorate hexahydrate per milliliter of n-propanol). The reference wavelength of the test solution is determined as described above and found to be 218.5 nm with a wavelength shift of 0.1 nm for a bandpass of from 2 to 6 nm. About 15 ml of the solution is placed in a 20 ml borosilicate glass vial and the vial is sealed shut with a Teflon lined cap. This packaged test solution is then opened and used to determine the wavelength accuracy of a Waters Associates Model M490 variable wavelength liquid chromatography detector using the procedure given in the Detailed Description of the Invention. The indicated wavelength of maximum absorbance is about 218.5 nm indicating that the indicated wavelength of detection of this individual detector is in proper calibration at 218.5 nm.

What is claimed is:

1. A method for determining the wavelength accuracy of a variable wavelength liquid chromatography spectrophotometric detector in the low UV range, the detector having a flow through detection cell and a means to vary the indicated wavelength of detection, which method comprises the steps of:
   (a) flowing a solution of terbium III ions in a nondetrimental solvent into the cell, the solution having a detectable concentration of terbium III ions:
   (b) varying the indicated wavelength of detection to find the indicated wavelength of maximum absorbance of the solution in a wavelength region around a predetermined reference wavelength for terbium III in the solvent: and
   (c) calculating the difference, in units of nm, between the indicated wavelength of maximum absorbance of step (b) and the reference wavelength of step (b) to determine the accuracy of the detector at the reference wavelength of step (b).

2. The method of claim 1 wherein the terbium III ions are generated from terbium III perchlorate and the concentration of terbium III perchlorate in the solvent is more than about one milligram per milliliter and less than about 5 milligrams per milliliter.

3. The method of claim 1 wherein the solvent is selected from the group consisting of ethanol, n-propanol, n-butanol, 2-propanol, 1,2-propanediol, tetrahydrofuran, 2-methoxyethylether, 2-ethoxyethanol, and 2-methoxyethanol.

4. The method of claim 2 wherein the solvent is selected from the group consisting of ethanol, n-propanol, n-butanol, 2-propanol, 1,2-propanediol, tetrahydrofuran, 2-methoxyethylether, 2-ethoxyethanol, and 2-methoxyethanol.

5. The method of claim 1 wherein the solvent is selected from the group consisting of ethanol, n-propanol, n-butanol, 1,2-propanediol, and 2-methoxyethanol.

6. The method of claim 2 wherein the solvent is selected from the group consisting of ethanol, n-propanol, n-butanol, 1,2-propanediol, and 2-methoxyethanol.

7. The method of claim 4 wherein the solvent is n-propanol.

* * * * *